(12) United States Patent
Veenhof

(10) Patent No.: US 12,144,552 B2
(45) Date of Patent: Nov. 19, 2024

(54) TESTING TISSUE VIABILITY FOR AN ANASTOMOSIS

(71) Applicant: VEENHOF MEDICAL DEVICES B.V., Maastricht (NL)

(72) Inventor: Alexander Arnold Frederik Adriaan Veenhof, Maastricht (NL)

(73) Assignee: VEENHOF MEDICAL DEVICES B.V., Maastricht (NL)

( * ) Notice: Subject to any disclaimer, the term of this patent is extended or adjusted under 35 U.S.C. 154(b) by 994 days.

(21) Appl. No.: 16/959,796

(22) PCT Filed: Jan. 7, 2019

(86) PCT No.: PCT/NL2019/050008
§ 371 (c)(1),
(2) Date: Jul. 2, 2020

(87) PCT Pub. No.: WO2019/135681
PCT Pub. Date: Jul. 11, 2019

(65) Prior Publication Data
US 2020/0337779 A1 Oct. 29, 2020

(30) Foreign Application Priority Data
Jan. 5, 2018 (NL) .................................... 2020240

(51) Int. Cl.
*A61B 34/10* (2016.01)
*A61B 5/00* (2006.01)
(Continued)

(52) U.S. Cl.
CPC ............ *A61B 34/10* (2016.02); *A61B 5/0053* (2013.01); *A61B 5/0205* (2013.01);
(Continued)

(58) Field of Classification Search
CPC ..... A61B 34/10; A61B 5/0053; A61B 5/0205; A61B 5/4884; A61B 5/6885;
(Continued)

(56) References Cited

U.S. PATENT DOCUMENTS 7,618,376 B2 11/2009 Kimball
10,624,616 B2 * 4/2020 Mukherjee ........... A61B 5/6843
(Continued)

FOREIGN PATENT DOCUMENTS

EP 3181040 A1 6/2017
JP 2002-224059 A 8/2002
WO WO2013006053 A1 1/2013

OTHER PUBLICATIONS

International Search Report and Written Opinion for corresponding International application No. PCT/NL2019/050008; dated Jun. 19, 2019 (13 pages).
(Continued)

*Primary Examiner* — Christine H Matthews
*Assistant Examiner* — Anna Roberts
(74) *Attorney, Agent, or Firm* — Mendelsohn Dunleavy P.C.

(57) ABSTRACT

A method is described for testing the viability of a tissue of a patient for an anastomosis using a perfusion measuring device wherein the method may comprise: controlling at least one actuating structure of the perfusion measuring device to rapidly ramp up a force exerted on at least one test area of the tissue selected for an anastomosis, the force exerted on the at least one test area defining a local (systolic) perfusion pressure; and, during the ramp up of the force, the computer receiving a sensor signal from at least one sensor of the perfusion measuring device and a signal from a blood pressure device, the sensor signal being indicative of perfusion of blood through the micro vascularization in the first (Continued)

test area and the blood pressure signal being indicative of a general (systolic) blood pressure of the patient; controlling the first actuating structure to slowly ramp down the force exerted on the first test area, when the sensor signal signals the computer that the perfusion of the blood in the tissue of the first test area has stopped; and, during the ramp down of the force, the computer determining the local perfusion pressure at which the sensor signal indicates a start of perfusion of blood through the micro vascularization, the determined local perfusion pressure defining a reperfusion pressure value of the first test area; and, determining a prediction whether or not the tissue of the at least one test area is viable for an anastomosis on the basis of the local reperfusion pressure value of the at least one test area and the general systolic blood pressure value.

24 Claims, 7 Drawing Sheets

(51) Int. Cl.
    A61B 5/0205    (2006.01)
    A61B 5/021     (2006.01)
    A61B 5/026     (2006.01)
    A61B 5/1455    (2006.01)
    A61B 17/11     (2006.01)
    G16H 40/60     (2018.01)
    G16H 50/20     (2018.01)

(52) U.S. Cl.
    CPC .......... *A61B 5/4884* (2013.01); *A61B 5/6885* (2013.01); *A61B 5/7275* (2013.01); *A61B 17/1114* (2013.01); *G16H 40/60* (2018.01); *G16H 50/20* (2018.01); *A61B 5/021* (2013.01); *A61B 5/0261* (2013.01); *A61B 5/14551* (2013.01)

(58) Field of Classification Search
    CPC ... A61B 5/7275; A61B 17/1114; A61B 5/021; A61B 5/0261; A61B 5/14551; A61B 5/4848; A61B 5/42; A61B 5/02233; G16H 40/60; G16H 50/20
    See application file for complete search history.

(56) References Cited

U.S. PATENT DOCUMENTS

| 10,687,811 B2* | 6/2020 | Evans ................ A61B 5/02158 |
| 2006/0287603 A1* | 12/2006 | Bartnik ................ A61B 5/0261 |
| | | 600/481 |
| 2008/0183059 A1 | 7/2008 | LaPlante et al. |
| 2009/0118628 A1* | 5/2009 | Zhou ................ A61B 5/1075 |
| | | 600/499 |
| 2014/0135604 A1 | 5/2014 | Cuesta Valentin et al. |
| 2015/0105810 A1 | 4/2015 | Leschinsky et al. |

OTHER PUBLICATIONS

Notice of Reasons for Refusal for corresponding Japanese application No. 2020-537650; dated Dec. 6, 2022 (13 pages).
Notice of Reasons for Refusal for corresponding Japanese application No. 2020-537650; dated Sep. 5, 2023 (9 pages).

* cited by examiner

TESTING TISSUE VIABILITY FOR AN ANASTOMOSIS

FIELD OF THE INVENTION

The invention relates to testing tissue viability for an anastomosis, and, in particular, though not exclusively, to methods and system for testing the viability of a tissue for an anastomosis and a computer program product for using such method.

BACKGROUND OF THE INVENTION

An anastomosis is a surgical connection between two structures, typically two tubular structures, such as blood vessels or loops of intestine. Anastomotic leakage is a serious complication following colorectal surgery. Its reported prevalence varies widely from 1% to 39%. Not only may the complication result in an acute life-threatening condition, cancer patients show a higher local recurrence rate following anastomotic complications with local abscess formation. Anastomotic complications are thought to be related to an inadequate perfusion of the anastomosis.

Before performing the anastomosis, viability of the bowel tissue is usually estimated by the color of the tissue. This remains very subjective and is based on the experience of the surgeon. Roughly 1.5 million patients undergo bowel surgery every year, resulting in approximately 150.000 anastomotic leakages. With a mortality rate of 8%, this subsequently means approximately 12.000 directly related deaths and immense anastomotic leakage related medical expenses.

WO2013/006053 describes a system and method for predicting the viability of a body tissue. The system includes a system for measuring a local perfusion pressure and a systemic perfusion pressure and determining an index on the basis of the measured pressures. The prior art system however does not provide a testing scheme for accurately predicting leakage after anastomosis of bowel tissue. In particular, the prior art system does not provide tissue viability testing system that is sufficiently accurate and reliable so that it may help a surgeon making a decision during surgery that includes anastomosis.

EP3181040 describes a surgical instrument including a sensor for measuring local perfusion in a tissue and a sensor for measuring the pressure applied to the tissue. The instrument includes pivotly connected jaw members for grasping and applying a force to the tissue. When using the jaw members to apply a pressure on the tissue, a non-uniform pressure is applied to the tissue, which makes a reliable and reproducible measurement of the local perfusion very difficult.

Hence, there is a need in the art for improved methods and systems for testing the viability of a tissue for an anastomosis. In particular, there is a need in the art for tissue viability test methods and systems that provide a reliable and accurate prediction of the risk of anastomosis leakage.

SUMMARY OF THE INVENTION

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit", "module" or "system." Functions described in this disclosure may be implemented as an algorithm executed by a microprocessor of a computer. Furthermore, aspects of the present invention may take the form of a computer program product embodied in one or more computer readable medium(s) having computer readable program code embodied, e.g., stored, thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by, or in connection with, an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by, or in connection with, an instruction execution system, apparatus, or device.

Program code embodied on a computer readable medium may be transmitted using any appropriate medium, including but not limited to wireless, wireline, optical fiber, cable, RF, etc., or any suitable combination of the foregoing. Computer program code for carrying out operations for aspects of the present invention may be written in any combination of one or more programming languages, including an object oriented programming language such as Java™, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor, in particular a microprocessor or central processing unit (CPU), of a general purpose computer, special purpose computer, or other programmable data processing apparatus to produce a machine, such that the instructions, which execute via the processor of the computer, other programmable data processing apparatus, or other devices create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

It is an objective of the invention to reduce or eliminate at least one of the drawbacks known in the prior art.

In an aspect, the invention may relate to a method for testing the viability of a tissue of a patient for an anastomosis using a perfusion measuring device comprising: a computer controlling at least one actuating structure of the perfusion measuring device to rapidly ramp up a force exerted on at least one test area of the tissue selected for an anastomosis, the force exerted on the at least one test area defining a local (systolic) perfusion pressure; and, during the ramp up of the force, the computer receiving a sensor signal from at least one sensor of the perfusion measuring device and a signal from a blood pressure device, the sensor signal being indicative of perfusion of blood through the micro vascularization in the first test area during the ramp up of the force and the blood pressure signal being indicative of a general (systolic) blood pressure of the patient during the ramp up of the force; when the sensor signal signals the computer that the perfusion of the blood in the tissue of the first test area has stopped, the computer controlling the actuating structure to slowly ramp down the force exerted on the first test area; and, when, during the ramp down of the force, the computer detects a start of perfusion of blood through the micro vascularization, the computer determining a local perfusion pressure value and a general blood pressure value for determining a prediction whether or not the tissue of the at least one test area is viable for an anastomosis, the determined local perfusion pressure value defining a local reperfusion pressure value of the first test area.

In an embodiment, the method may further comprise: the computer determining a prediction whether or not the tissue of the at least one test area is viable for an anastomosis on the basis of the local reperfusion pressure value of the at least one test area and the general systolic blood pressure value.

In an embodiment, the determination of the prediction may include: comparing the ratio of the local reperfusion pressure value and the general systolic blood pressure value with a predetermined index value stored in a memory of the computer.

Hence, the invention provides an improved method for testing the viability of a tissue of a patient for an anastomosis using a perfusion measuring device. In contrast to the prior art, the method includes a computer controlling of the force exerted on a tissue including a steep pressure build up until the maximum perfusion pressure and slow-release of the pressure in order to measure the pressure at which reperfusion occurs. During the relatively fast force ramp up and the relatively slow force ramp down the local perfusion pressure of the test area is measured and compared with a general blood pressure of the patent. This way a highly reliable tissue viability testing system can be realized which is sufficiently accurate and reliable so that it may help a surgeon in making decisions during surgery that includes anastomosis In an embodiment, determining a prediction includes: comparing the ratio of the local reperfusion pressure value and the general systolic blood pressure value with a predetermined index value stored in a memory of the computer. In an embodiment, the tissue may be a bowel tissue. In another embodiment, the blood pressure signal may be indicative of the (systolic) blood pressure of the patient measured at the arm. In an embodiment, determining a prediction may include: determining that bowel tissue of the at least one test area is viable for an anastomosis if the ratio of the local reperfusion pressure value and the general systolic blood pressure value is equal to or larger than a predetermined bowel-brachial index threshold value, preferably the threshold value being selected between 0.1 and 0.5, more preferably between 0.2 and 0.4, even more preferably (approximately) 0.3. Hence, the index measured by the test process may be compared with an index threshold value and based on this comparison a very accurate prediction can be obtained whether the test area of the tissue is viable for an anastomosis.

Hence, the tissue viability testing system can be used as an efficient and accurate system for predicting the healing capability of an anastomosis. For example, in an embodiment, the computer system may determine an index, such as the bowel-brachial index, and determine whether the index is smaller, equal or larger than a predetermined index threshold value. The computer may display the measured index and, optionally, a recommendation associated with the measured index on the screen. This way, the index determined by the system provides a surgeon in insight in the occurrence of anastomotic leakage based on ischemic post-operative problems with a positive predictive value of between 86% and 89%. If the system determines that the bowel-brachial index is below the index threshold value, the surgeon may choose to take action.

An operating surgeon may evaluate if the bowel can be mobilized further and a segment of bowel nearer to the main artery stem may be found with a higher bowel-brachial index followed by a safe anastomosis. If the bowel cannot be (further) mobilized and an adequate bowel-brachial index cannot be obtained, the surgeon may choose to protect the anastomosis by a deviating stoma if the patient is fit enough to survive a potential anastomotic leakage. In case the index is equal or larger than the index threshold value the anastomosis cannot be determined and the patient has severe comorbidity (and potentially would not survive an anastomotic leakage), a permanent stoma may be considered.

In an embodiment, a first time period for the ramp up from atmospheric pressure to a maximum perfusion pressure value at which minimal or no blood perfusion is measured by the sensor is smaller than a second time period for the ramp down from the maximum perfusion pressure to the atmospheric pressure. In an embodiment, the first time period may be selected between 2 and 20 second; and, the second time period for the ramp down from the maximum perfusion pressure to an atmospheric pressure may be selected between 3 and 60 seconds. In an embodiment, the second period may be selected to be at least 1.5 times the first period, preferably 2 times the first period, more preferably 4 times the first period.

In an embodiment, the actuating structure may comprise a pressure plate, preferably a slidable pressure plate, for exerting a force uniformly downwards onto tissue of the at least one test area that is positioned between the pressure plate and a clamping member of the perfusion measuring device, preferably the surface of the pressure plate being arranged parallel to the surface of the clamping member.

In an embodiment, the actuating structure may include a pressure chamber connected to the slidable pressure plate, wherein the pressure in the pressure chamber controls the force exerted onto the tissue, preferably the computer controlling a pump for controlling the pressure in the pressure chamber.

In an embodiment, the linear actuating structure may comprise a bellow structure, preferably a linearly expandable bellow structure, or the linear actuating structure comprising an expandable balloon structure.

In an embodiment, a sliding structure may slidably connecting the pressure plate to the housing to to keep the surface of the pressure plate parallel to the surface of the second clamping member. This way, during operation of the perfusion measuring device, a uniform pressure may be applied to the tissue. Uniform application of pressure to the tissue is important for obtaining reliable and reproducible measurements of the perfusion.

In an embodiment, the sensor may an optical sensor. In an embodiment, the optical sensor may be integrated in the clamping member. In an embodiment, the optical sensor may be implemented as a reflective type optical sensor. In yet another embodiment, the optical sensor may be adapted to measure absorption of light emitted onto the tissue of the first test area during the ramp up and the ramp down.

In an embodiment, the method may further include: during at least part of the ramp up and the ramp down, the computer receiving a motion signal of a motion sensor, preferably a (3D) accelerometer, attached to the perfusion measuring device; and, the computer rejecting or accepting the measured local reperfusion pressure value on the basis of the motion signal and a predetermined motion threshold value. Hence, in this embodiment, if the motion does exceed the threshold value, the computer may reject the measured data and warn the user to execute the testing process again. If not the computer may accept the measured data and determine the prediction. This way, the system is able to reliably measure a sensor signal and to determine the pressure value $p_r$ at which reperfusion occurs.

In a further aspect, the invention may relate to a system for testing the viability of a tissue of a patient for an anastomosis comprising: a computer that is connectable to a perfusion measuring device, the computer including a computer readable storage medium having computer readable program code embodied therewith, and a processor, preferably a microprocessor, coupled to the computer readable storage medium, wherein responsive to executing the first computer readable program code, the processor is configured to perform executable operations comprising: controlling at least one actuating structure of the perfusion measuring device to rapidly ramp up a force exerted on at least one test area of the tissue selected for an anastomosis, the force exerted on the at least one test area defining a local (systolic) perfusion pressure; and, during the ramp up of the force, the computer receiving a sensor signal from at least one sensor of the perfusion measuring device and a signal from a blood pressure device, the sensor signal being indicative of perfusion of blood through the micro vascularization in the first test area during the ramp up of the force and the blood pressure signal being indicative of a general (systolic) blood pressure of the patient during the ramp up of the force; controlling the actuating structure to slowly ramp down the force exerted on the first test area when the sensor signal signals the computer that the perfusion of the blood in the tissue of the first test area has stopped, and, determining a local perfusion pressure value and a general blood pressure value when, during the ramp down of the force, the computer detects a start of perfusion of blood through the micro vascularization, the local perfusion pressure value and a general blood pressure value being used for determining a prediction whether or not the tissue of the at least one test area is viable for an anastomosis, the determined local perfusion pressure value defining a local reperfusion pressure value of the first test area.

In a further embodiment, the executable operations may include: determining a prediction whether or not the tissue of the at least one test area is viable for an anastomosis on the basis of the local reperfusion pressure value of the at least one test area and the general systolic blood pressure value, preferably the determination of the prediction including: comparing the ratio of the local reperfusion pressure value and the general systolic blood pressure value with a predetermined index value stored in a memory of the computer.

Hence, in this embodiment, a tissue that needs to be tested for an anastomosis may be positioned between the clamping member and the actuating structures. This way, each of the actuating structures may be used to test a different area of the tissue. Hence, a plurality of areas may be efficiently tested sequentially by the computer. During testing, each actuating structure may be controlled on the basis of the processes described in this applications. This way, the local viability of a plurality of areas can be tested efficiently. Moreover, if the computer determines that a first test area is not viable for an anastomosis, other areas may be tested without the need to shift the tissue that is clamped.

In other embodiments, the perfusion measuring device may be part of or integrated in another medical device. In an embodiment, the perfusion measuring device may be part of a surgical stapling device for attaching tissues to each other during surgery. In an embodiment, the stapling device may include clamping members that include an actuating structure and a perfusion sensor similar to the perfusion measuring device as described with reference to the embodiments of this application. The first clamping member may further include a stapling mechanism and the second clamping member may function as an anvil for receiving a staple during a stapling action of the stapling mechanism.

Hence, the stapling device may include a perfusion measuring device that is capable of applying a predetermined pressure to the tissue and measuring the blood perfusion at such pressure. Using such stapling device, a surgeon is able to test the viability of a test area of the tissue and thereafter use its stapling mechanism to attach two parts of tissue if the viability of the tissue is sufficient. Moreover, such stapling device may use the same processes as described with reference to the embodiments in this application, in which tissue is fixated between the clamping members and pressurized until no perfusion is detected by the perfusion sensor. Thereafter, the pressure is slowly released until reperfusion is detected. The system may keep the tissue at a pressure at which the reperfusion is detected and then staple the tissue so that the tissue is fixed by the staples at a pressure that allows some blood perfusion. This will stimulate healing of the wound.

The invention will be further illustrated with reference to the attached drawings, which schematically will show embodiments according to the invention. It will be understood that the invention is not in any way restricted to these specific embodiments.

DETAILED DESCRIPTION

Figure 1A:
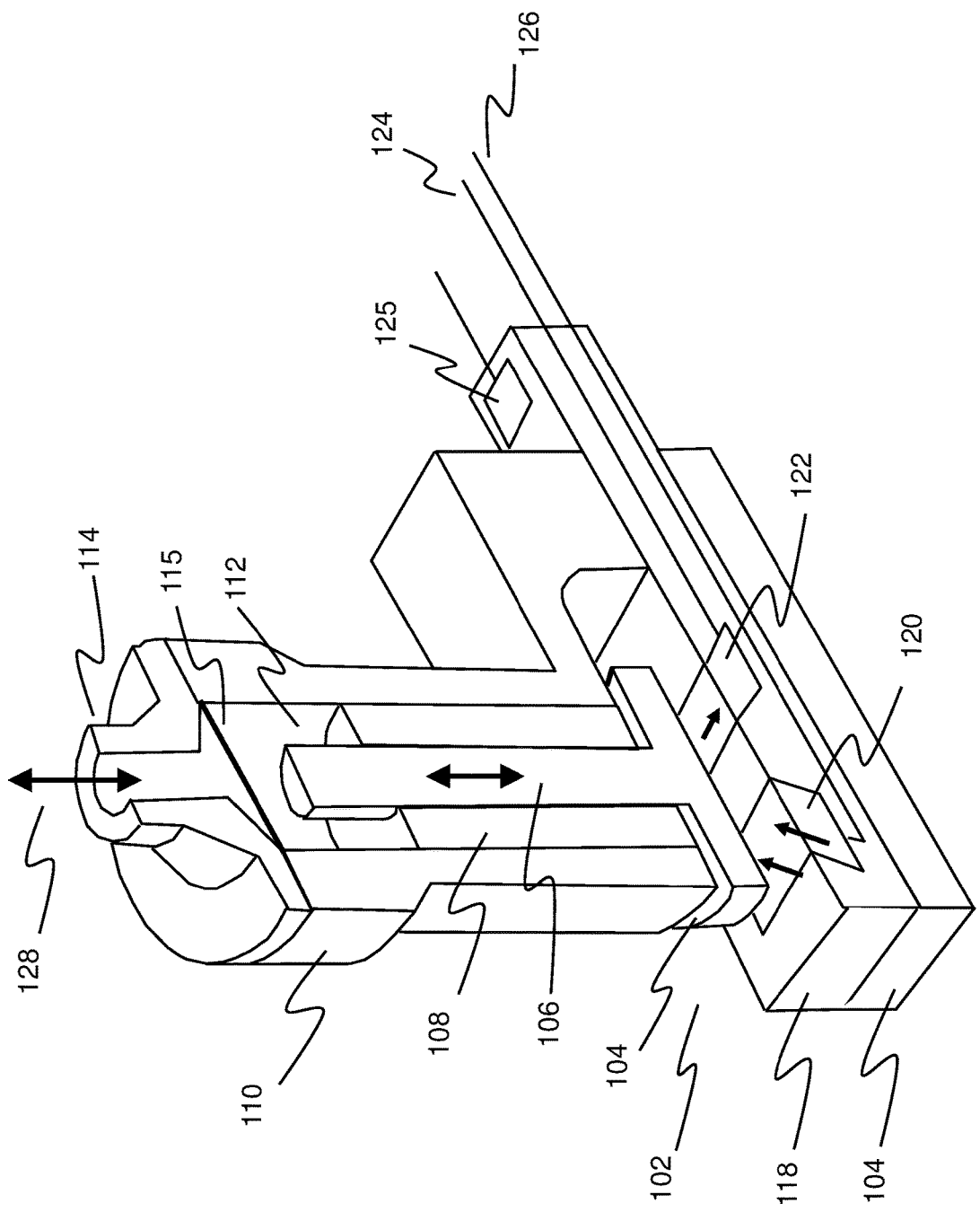
FIGS. 1A and 1B schematically depict perfusion measuring devices used in the embodiments of this application.

FIG. 1A schematically depicts an anastomosis perfusion measuring device which may be used in the embodiments of this application. Such device may include a first clamping member 102 that is positioned to a second clamping member 104 so that a tissue can be fixated between the flat surfaces of the two clamping members. To that end, the first clamping member 102 may include an actuating structure that may include a (rectangular) pressure plate 104 and a guiding means for guiding a surface of the pressure plate that is contact with the tissue towards a surface of the second clamping member. For example, in an embodiment, the pressure plate may be part of a structure that has the shape of a plunger 106, that is slideable arranged in a sleeve 108 which is positioned in a housing 110, which may include a chamber for housing an actuating structure. The pressure plate may have an area selected between 0.25 and 10 cm$^2$, preferably between 0.5 and 5 cm. The plunger may be operable connected to the actuating structure, preferably a linear actuating structure.

In an embodiment, the actuating structure may be a pneumatic actuating structure. In that case, the actuating structure may include a pressure chamber 112 wherein the pressure chamber includes a connector 114 for attaching a pressure line which may be connected to a pump. In an embodiment, the pressure chamber may include a membrane 115 which may improve the fluid tightness of the pressure chamber. The pressure chamber may be operatively connected to the pressure plate (through the membrane) in order to exert pressure on the pressure plate when the pressure in the pressure room is above ambient pressure. In an embodiment, the pressure plate may be part of a plunger structure.

Instead of an actuator, which is controlled by air pressure (a pneumatic actuator), other types of actuators may also be used. For example, in an embodiment, the linear actuator may be implemented as electro-mechanical actuator including a linear motor for moving a slidable pressure plate. In that case, the linear motor may be connected to a controller for controlling the linear motor. In a further embodiment, the linear actuator may be implemented as a hydraulic actuator including a hollow cylinder having a piston inserted in it.

In an embodiment, the second clamping member 116 may be connected to the housing so that the first clamping member can move relative to the second clamping member by controlling the linear actuating structure, e.g. by controlling a pump to change the pressure in the pressure chamber. A tissue, e.g. bowel tissue, (not shown) may be positioned between the first and second clamping member and fixated by the clamping members by moving the first clamping member towards the second clamping member. The first or second clamping member may include a perfusion sensor 118 which is configured to measure blood perfusion through the tissue when pressure is applied to the tissue. The blood perfusion may be measured on the basis of the optical response of the tissue.

The optical response may be measured by exposing the tissue to the light of a light emitting device 120, e.g. a laser or a LED, and an optical sensor 122, e.g. a photodiode, measuring the light originating from the tissue. Based on the optical response of the tissue, the blood perfusion through the tissue as a function of the pressure applied to the tissue may be measured. The perfusion is measured at the position where pressure is exerted on the tissue, so there is a direct relationship between the pressure on the tissue and perfusion of the blood through the tissue.

Figure 1B:
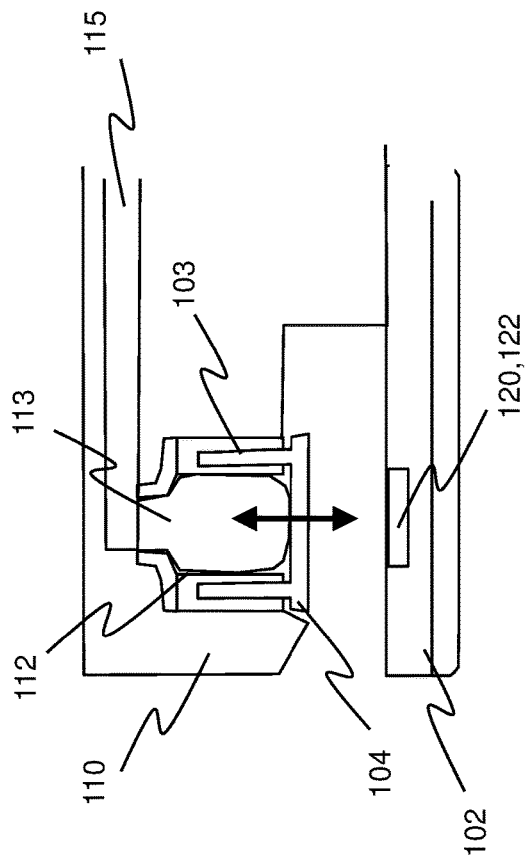

FIG. 1B schematically depicts a cross-sectional view of anastomosis perfusion measuring device according to an embodiment of the invention. The device may comprise a housing 110 comprising a first clamping member 104 (preferably in the form of a pressure plate), a second clamping member 102 and a pressure chamber 112. The second clamping member has a surface in which an optical sensor for measuring the perfusion is embedded. The pressure chamber may comprise a balloon 113 which is connected via a pressure line 115 to a pump so that it can be controllable inflated and deflated. The balloon may be contained in the pressure chamber and may be in contact or connected to a pressure plate 104, which is slidable connected to the housing. To that end, pressure plate may include a sliding structure 103 so that the surface of the pressure plate can be moved towards the surface of the first clamping member while keeping the surface of the pressure plate parallel to the surface of the second clamping member. When inflating the balloon, the expanding balloon will press the pressure plate towards the flat surface of the second clamping member.

As shown in FIGS. 1A and 1B, the sliding structure which slidably connects the pressure plate to the housing is arranged to keep the surface of the pressure plate parallel to the surface of the second clamping member. This way, during operation of the perfusion measuring device, a uniform pressure may be applied to the tissue. Uniform application of pressure to the tissue is important for obtaining reliable and reproducible measurements of the perfusion.

In an embodiment, the blood perfusion may be measured using an SpO2 sensor. SpO2 stands for peripheral capillary oxygen saturation, which provides an estimate of the amount of oxygen in the blood. An SpO2 sensor is an opto-electronic sensor including one or more light emitting devices, e.g. LEDs, adapted to emit light of a predetermined wavelength or a predetermined band of the electro-magnetic spectrum onto a tissue and one or more light sensors, e.g. photodiodes, adapted to receive LED light that is reflected from the tissue or transmitted through tissue. In particular, light emitting diodes may expose part of the tissue to red and infrared light and one or more light detectors, e.g. a photodiode.

The amount of light received by the detector provides an indication of the amount of oxygen bound to the hemoglobin in the blood. Oxygenated hemoglobin (oxyhemoglobin or HbO2) absorbs more infrared light than red light and deoxygenated hemoglobin (Hb) absorbs more red light than infrared light. Thus, by detecting the amount of red and infrared light transmitted through or reflected from the tissue an SpO2 value may be determined.

Optical perfusion sensors, such SpO2 sensor, are very sensitive to motion, which may introduce noise and artifacts in the signal that is generated by the sensor. Such motion noise may thus produce measured data that are not suitable for determining a reliable prediction regarding the viability of the tissue that is tested. Hence, in an embodiment, the anastomosis perfusion measuring device may comprise a motion sensor 125, e.g. a (digital) (3D) accelerometer, that may be configured to generate motion data representing a measure of the motion of the perfusion measuring device when a tissue is tested.

Figure 2:
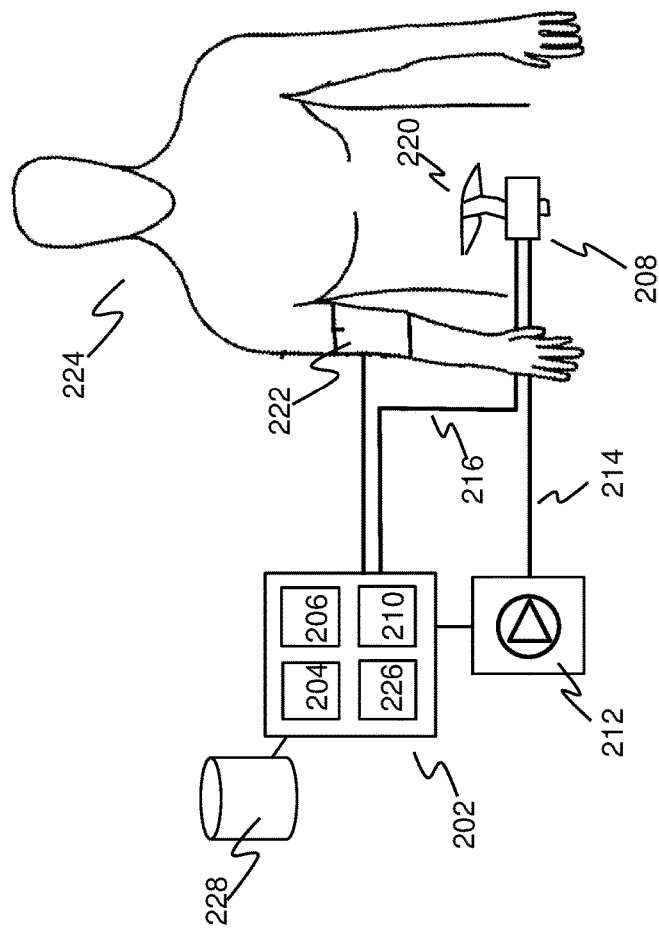
FIG. 2 schematically depicts a tissue viability testing system for an anastomosis according to an embodiment of the invention.

FIG. 2 schematically depicts a tissue viability testing system for an anastomosis according to an embodiment of the invention. The system is adapted to determine a measure of the viability of tissue, such as the viability of bowel tissue, for an anastomosis. Based on this measure the system determines a reliable prediction for the occurrence of anastomotic leakage, if the measured tissue is used for the anastomosis.

The system may comprise a computer 202 comprising a processor 204 connected to a memory 206. Software code portions may be stored in the memory wherein the code portions are configured for, when executed by the processor, controlling a perfusion measuring device 208 (e.g. a perfusion measuring device as described with reference to FIG. 1) for testing the viability of a tissue during the operation of a patient 210 and a blood pressure measuring device 212 for measuring the blood pressure of the patient during the testing. The computer may receive measured values of the perfusion measuring device and the blood pressure measuring device and use this information to determine if leakage of an anastomosis is highly likely to occur. The details of the testing process executed by the computer is described hereunder in greater detail.

Figures 3A, 3B, 3C:
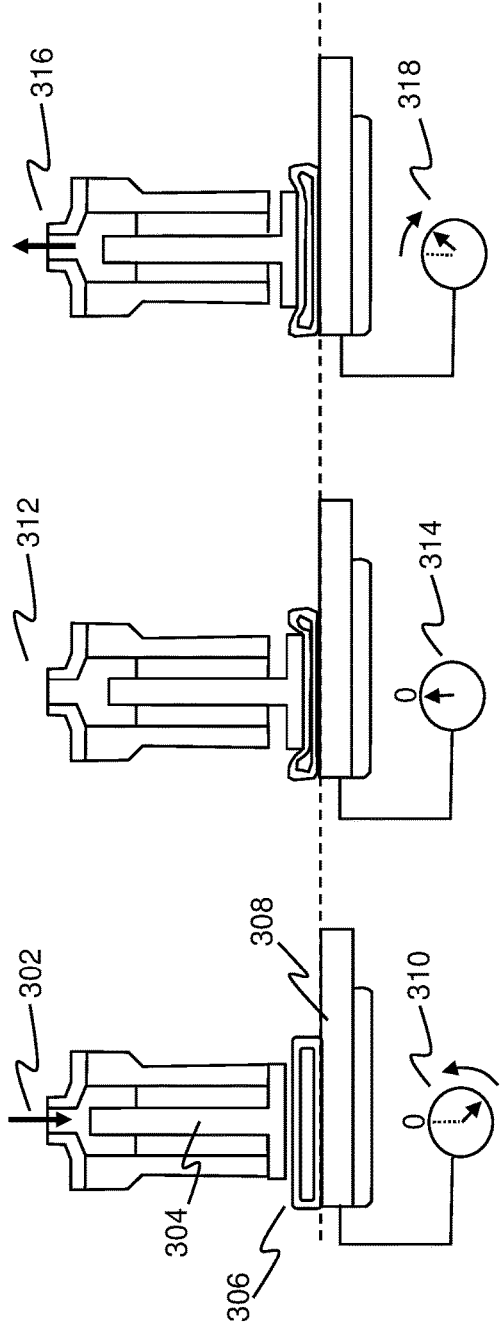
FIG. 3A-3C depicts a process for testing the viability of tissue for an anastomosis according to an embodiment of the invention.

During operation, a surgeon may place part an area of the bowel wall within the perfusion measuring device and start a testing process for testing the viability of an area of the bowel tissue. An example of a testing process is depicted in FIG. 3A-3C. The process may be executed using a tissue viability testing system as described with reference to FIG. 2. A surgeon may position a tissue between the clamping members of the measuring device and execute a measuring cycle. The process may include a computer receiving a start signal to start the testing process, e.g. the surgeon instructing the computer to start the process. In response to the start signal, the computer may control the actuator of the perfusion measurement device to move one of the first clamping member in the form of a pressure plate (e.g. a slidable plunger or the like), onto the tissue. For example, in an embodiment, the computer may control a pump to increase the pressure 302 in the pressure chamber of the perfusion measuring device. Increasing the pressure will move the slidable pressure plate 304 downwards onto the tissue that is positioned between clamping members of the perfusion measuring device. Thus, the computer may control the actuating structure of the device to ramp up a force that is uniformly applied by a clamping member to the tissue 306. During the ramp-up, the computer monitors, preferably continuously, the perfusion through the tissue.

During the testing process, the computer may control the force exerted on the tissue as a function of the sensor signal generated by the perfusion sensor. This signal sensor correlates with the amount of blood that flows through the micro vascularization of the bowel wall. The force that is uniformly exerted on the tissue as a function of time may follow or may approximately follow a curve as depicted in FIG. 4.

Upon start, at a first time instance $t_0$, the computer may rapidly ramp up the pressure exerted onto the tissue. For example, the computer may rapidly ramp up the pressure in the pressure chamber, which correlates with the force exerted on the tissue. This way, the force exerted on the tissue rapidly increases so that the sensor signal 310 will indicate that the perfusion through the micro vascularization rapidly decreases (see FIG. 3A). During the pressure ramp up 402, the perfusion through the tissue may be monitored. The computer may ramp up the pressure up to a predetermined maximum perfusion pressure $p_m$ 403 at which the perfusion has stopped and at which the blood fluids has been squeezed out of the micro vascularization in the testing area, i.e. the area of the tissue where the force is applied (see FIG. 3B). At the same time, the computer may control a pressure sensing device to measure the systolic blood pressure of the patient at a predetermined location, e.g. the arm.

The time period $t_0$-$t_1$ in which the force exerted on the tissue is increased from a first pressure, e.g. atmospheric pressure, to the maximum perfusion pressure $p_m$ may be selected such that the force only affects the blood fluids in the micro vascularization of the bowel wall, but not the intercellular fluids in the bowel wall. To that end, a fast pressure ramp up may be selected. In an embodiment, the time period $t_0$-$t_1$ for the ramp up (from atmospheric pressure to a maximal perfusion pressure at which minimal or no blood perfusion is measured) may be selected in a range between 2 and 20 seconds. In an embodiment, values for the maximum perfusion pressure may be selected in a range between 0 and 120 mmHg.

Figure 4:
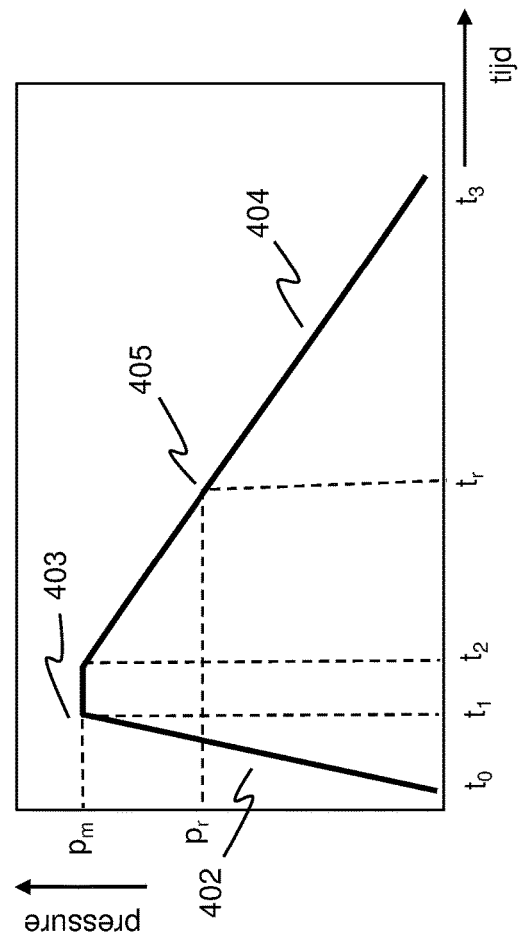
FIG. 4 schematically depicts a process for controlling the pressure applied to a tissue by a perfusion measuring device according to an embodiment of the invention.

Thereafter, as shown in FIG. 4 at a third time instance t2 the computer may start to slowly ramp down 402 the pressure so that the force exerted on the tissue is slowly released, thus allowing the capillary blood vessels to be filled with blood and to start to blood flow again. The time period for the pressure ramp down from the maximum perfusion pressure to an atmospheric pressure may smaller than the time period for the pressure ramp up. In an embodiment, this period may be selected in a range between 3 and 60 seconds. During the ramp down, the computer may determine based on the sensor signal 318 that perfusion through the tissue has started again (see FIG. 3C). The time instance (which may be referred to as the reperfusion time instance $t_r$) at which reperfusion is detected may occur at a reperfusion pressure $p_r$ 405. The pressure value $p_r$ (in mmHg) at which reperfusion occurs is determined by the processor and stored in a memory connected to the processor.

During execution of the testing process, in particular the period around which reperfusion is detected, the computer further controls a blood pressure device to measure the systolic blood pressure value. The blood pressure may be measured at the brachial artery at the arm. Thereafter, the computer may determine an index as a ratio between the measured reperfusion pressure $p_r$ (in mmHg) at the bowel wall and the systolic blood pressure (in mmHg) at the arm. There the pressure may be measured in terms of mmHg or any other suitable unit. This index may be referred to as the bowel-brachial index.

In a further embodiment, during the testing process, the motion of the device may be measured using a motion sensor that is attached to the perfusion measuring device. The computer may receive the motion information and check if the motion that is measured during the testing process, in particular around the reperfusion time instance $t_r$, is not exceeding a particular threshold value. If the motion does exceed this threshold value, the computer may reject the measured data and warn the user to execute the testing process again. This way, the system is able to reliably measure a sensor signal and to determine the pressure value $p_r$ at which reperfusion occurs.

As will be shown hereunder in more detail, the control of the force uniformly exerted on a tissue by the pressure plate on the basis of the curve depicted in FIG. 4, i.e. a steep pressure build up until the maximum perfusion pressure and slow-release of the pressure in order to measure the pressure at which reperfusion occurs, may be used to realize a highly reliable tissue viability testing system which is sufficiently accurate and reliable so that it may help in making decisions during surgery that includes anastomosis.

Although FIG. 1-4 describe a stand-alone perfusion measuring device and its operation, the invention is not limited to such devices. In other embodiments (not shown), the perfusion measuring device may be part of or integrated in another medical device. For example, the perfusion measuring device may be part of a surgical stapling device for attaching tissues to each other during surgery. In an embodiment, the stapling device may include clamping members that include an actuating structure and a perfusion sensor similar to the perfusion measuring device as described with reference to the embodiments of this application. The first clamping member may further include a stapling mechanism and the second clamping member may function as an anvil for receiving a staple during a stapling action of the stapling mechanism.

Hence, the stapling device may include a perfusion measuring device that is configured to apply a predetermined pressure to the tissue and measuring the blood perfusion at such pressure. Using such stapling device, a surgeon is able to test the viability of a test area of the tissue and thereafter use its stapling mechanism to attach two parts of tissue if the viability of the tissue is sufficient. Moreover, such stapling device may use the same process as described with reference to FIG. 4, in which tissue is fixated between the clamping members and pressurized until no perfusion is detected by the perfusion sensor. Thereafter, the pressure is slowly released until reperfusion is detected. The system may keep the tissue at a pressure at which the reperfusion is detected and then staple the tissue so that the tissue is fixed by the staples at a pressure that allows some blood perfusion. This will stimulate healing of the wound.

The system as described with reference to FIG. 1-4 was tested in an animal model for safety and reproducibility. The system was found to produce similar bowel-brachial indexes at different sites on the bowel and at different time intervals. No damage to the bowel tissue in the animal model could be objectified. The device was shown to adequately measure a bowel-brachial index. However, additional clinical research was needed to investigate if the bowel-brachial index would be predictive for the occurrence of anastomotic leakage.

The bowel-brachial index was measured in 215 patients (of at least 18 years old) undergoing elective colorectal surgery with a primary anastomosis. Laparoscopic and open surgery for both malignant and benign indications were included. Palliative surgery and emergency surgery were exclusion criteria. Patients were included in four Dutch medical centers and operated by dedicated gastrointestinal surgeons. Measurement were blinded for the investigators, the bowel-brachial index displayed by the system was sealed until inclusion was stopped. Patient case record forms were cross-checked and signed by independent investigators.

Following resection of the diseased bowel, just prior to making the anastomosis, the bowel-brachial index measurements were taken on the remaining healthy bowel ends, which would subsequently be connected to form the anastomosis. Measurement were taken opposite of the mesenterium as this would be the location of minimum perfusion in the bowel wall. The bowel-brachial index was recorded per patient. Subsequently patients were followed for clinical signs of anastomotic leakage. If an anastomotic leakage was suspected an abdominal CT scan with intravenous and oral contrast was made.

An anastomotic leakage event may be defined as 1) anastomotic leakage objectified during re-operation; and, 2) contained anastomotic leakage objectified on abdominal CT scan with extravasation of endoluminal contrast not requiring re-operation. Further, an additional anastomotic event may be defined as: additional resection during initial surgery of bowel due to inadequate perfusion or ischemia, which was visually determined by the surgeon.

The study further included determining if the measured bowel-brachial index, preferably the lowest measured bowel-brachial index per patient during surgery was predictive for the development of postoperative anastomotic leakage or an additional event as described above.

Statistical analysis was performed using a SPSS software package (SPSS 23; SPSS, Chicago, IL, USA). Medians, means, percentages and ranges were calculated and subsequently depicted when appropriate. Chi-square tests, Kruskal-Wallis tests and ANOVA tests were applied for group comparison when appropriate. Significance was set at $p<0.05$ In total 237 patients were included into the prospective blinded trial. In 22 patients, the bowel-brachial index could not be measured during surgery for a variety of reasons, which are depicted in Table 1.

TABLE 1 reasons for exclusion from measurements

|  | Reasons index not measured (22 patients) |
|---|---|
| Defective APM device | 6 |
| No surgical resection possible | 3 |
| Intra-corporeal anastomosis | 7 |
| No anastomosis possible, stoma instead | 5 |
| Bowel too fragile for measurement | 1 |

The bowel-brachial index was subsequently successfully measured in 215 patients, 114 (53%) men and 101 (47%) women.

Further patient and surgery characteristics are depicted in Table 2.

TABLE 2 patient characteristics

|  | Measured Patients (215) |
|---|---|
| Gender | 114 (53%) men/101 (47%) women |
| Age | 69 (35-91) |
| BMI | 26.9 (19-45) |
| ASA classification | |
| 1 | 40 (19%) |
| 2 | 123 (57%) |
| 3 | 52 (24%) |
| Type of Anastomosis | |
| stapled | 129 (60%) |
| suture | 86 (40%) |
| Type of Resection | |
| right colectomy | 104 (48%) |
| left colectomy | 55 (26%) |
| low anterior resection (<15 cm from anal verge) | 42 (20%) |
| small bowel resection | 14 (6%) |

Figure 5:
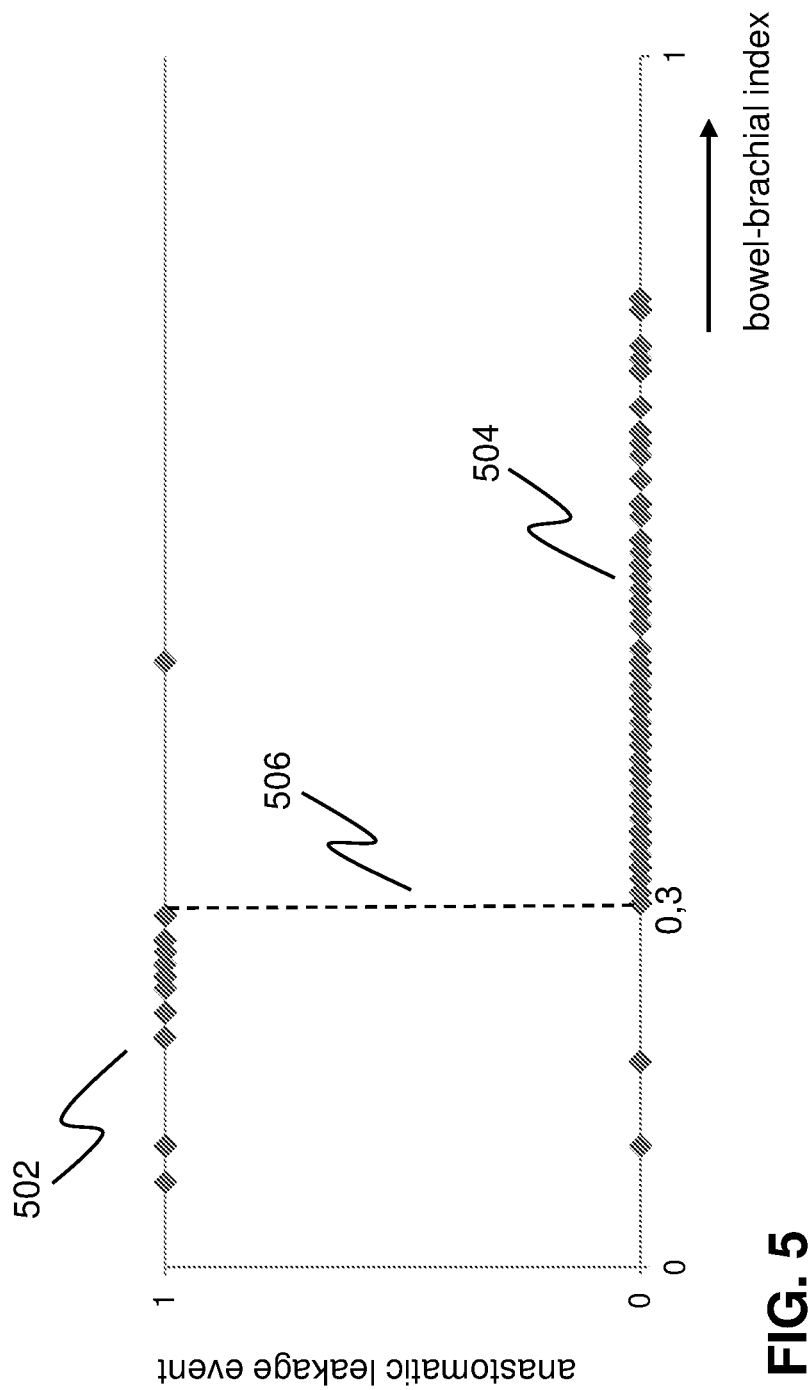
FIG. 5 depicts a graph of detected anastomotic leakage events as a function of measured bowel-brachial indices.

The results of the measured index and its correlation with an anastomotic event is depicted in FIG. 5. As shown in this figure, the inventors surprisingly found that the measurements generated by the tissue viability testing system show a high number of anastomotic leakage events below a predetermined index number and a very low number of anastomotic leakage events. As shown in the figure, the data follow a step function wherein at a predetermined index threshold value the chance of a leakage event becomes very small. In this particular case, the testing of a bowel tissue, the index number threshold was determined to be approximate 0.3. Such reliable results could only be generated when the testing process was executed according to the process described with reference to FIG. 3A-3C and FIG. 4.

In total 17 (7.9%) anastomotic events were found wherein four (1.9%) extra resections due to bowel ischemia during surgery and 13 (6%) due to anastomotic leakages. As shown in FIG. 5, the critical bowel-brachial index threshold for detecting such event (an anastomotic leakage) was determined to be lower than 0.3. In 16 of the 18 patients with a bowel-brachial index of below 0.3 an anastomotic event took place. As shown in table 3 thereunder, for 196 of the 197 patients with a bowel-brachial index of 0.3 or higher, no anastomotic event took place and the anastomosis healed well. Significantly more patients had a problem with the anastomosis with a bowel-brachial index of below 0.3 (p<0.001). This provided a positive predictive value of 89% for the bowel-brachial index measured by the APM system on the occurrence of anastomotic events. Sensitivity is 94% and specificity is 98%.

TABLE 3 bowel-brachial index 0.3 threshold
(p < 0.001) for all anastomotic events

|  | Anastomotic Event | No Anastomotic Event |
|---|---|---|
| Bowel-brachial index < 0.3 | 16 | 2 |
| Bowel-brachial index ≥ 0.3 | 1 | 196 |

Analysis for only anastomotic leakage, excluding the patients with an extra resection due to per-operative ischemia, is depicted in table 4 below. For 12 of the 14 patients with a measured bowel-brachial index value below 0.3, an anastomotic leakage took place. In 196 of the 197 patients with a bowel-brachial index of 0.3 or higher, no anastomotic event took place and the anastomosis healed well. Significantly more patients exhibited an anastomotic leakage with a bowel-brachial index value below 0.3 (p<0.001). These measurements provide a positive predictive value of 86% for the bowel-brachial index measured by the system on the occurrence of postoperative anastomotic leakage (including a sensitivity of 92% and a specificity of 98%).

TABLE 4 bowel-brachial index 0.3 threshold
(p < 0.001) for anastomotic leakages only

|  | Anastomotic Leakage | No Anastomotic Leakage |
|---|---|---|
| Bowel-brachial index < 0.3 | 12 | 2 |
| Bowel-brachial index ≥ 0.3 | 1 | 196 |

The mean postoperative admittance for the 215 patients was 10 days (2-150). Complications not relating to anastomotic leak were observed in 50 (23%) patients (wherein more than one complication per patient can occur) and are depicted in Table 5. Mortality was observed in 2 (1%) patients, one due to myocardial infarction and the other due to a severe pneumonia.

TABLE 5 complications not relating to anastomotic leak

|  | Number of patients |
|---|---|
| Ileus | 21 |
| Pneumonia | 16 |
| Wound infection | 14 |
| Urinary tract infection | 4 |
| Myocardial | 3 |
| Pulmonary artery embolism | 2 |
| Trocar hernia | 1 |

While in the above-mentioned test the bowel-brachial index threshold was determined to be 0.3, other test data and/or device parameter may cause deviations from the experimentally determined value. Hence, from the above it follows that the tissue viability testing system can be used as an efficient and accurate system for predicting the healing capability of the bowel and anastomosis. For example, in an embodiment, the computer system may determine an index, such as the bowel-brachial index, and determine whether the index is smaller, equal or larger than a predetermined value. In an embodiment, the bowel-brachial index threshold may be between 0.1 and 0.5, preferably between 0.2 and 0.4, more preferably approximately 0.3. The computer may display the measured index and, optionally, a recommendation associated with the measured index on the screen. This way, the bowel-brachial index determined by the system provides a surgeon in insight in the occurrence of anastomotic leakage based on ischemic postoperative problems with a positive predictive value of between 86% and 89%. If the system determines that the Bowel-Arm index is below the bowel-brachial index threshold value, the surgeon may choose to take action.

An operating surgeon may evaluate if the bowel can be mobilized further and a segment of bowel nearer to the main artery stem may be found with a higher bowel-brachial index followed by a safe anastomosis. If the bowel cannot be (further) mobilized and an adequate bowel-brachial index cannot be obtained, the surgeon may choose to protect the anastomosis by a deviating stoma if the patient is fit enough to survive a potential anastomotic leakage. In case a bowel-brachial index that is equal of higher than the bowel-brachial index threshold value cannot be determined and the patient has severe comorbidity (and potentially would not survive an anastomotic leakage), a permanent stoma may be considered.

Figure 6B:
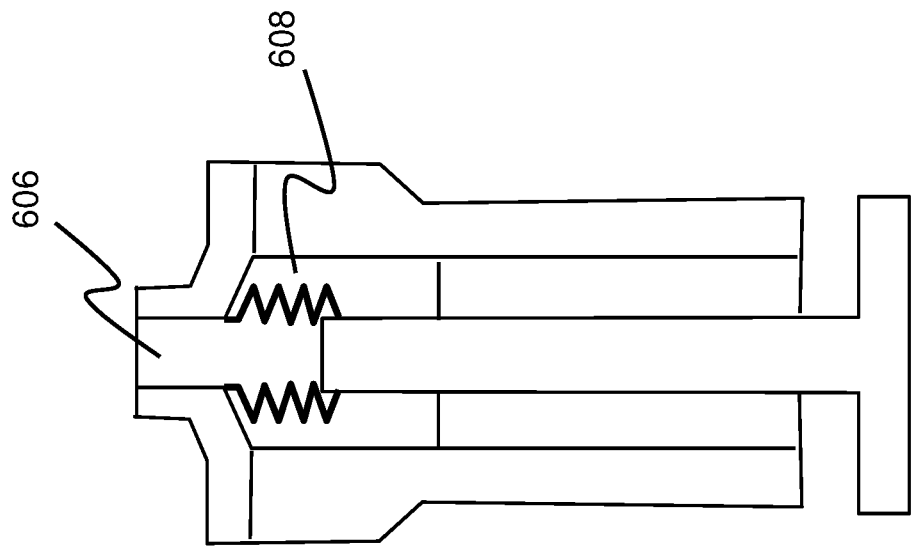
FIGS. 6A and 6B depict part of a perfusion measuring device according to another embodiment of the invention.
Figure 6A:
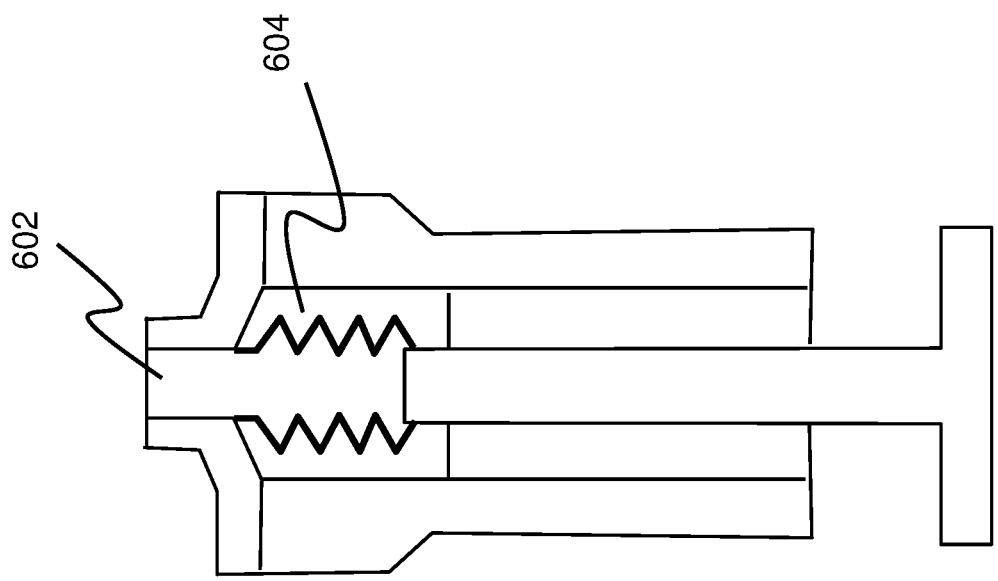

FIGS. 6A and 6B depict part of an anastomosis perfusion measuring device according to another embodiment of the invention. In this particular embodiment, an expandable element including a foldable structure that allow expansion in one direction, e.g. a bellows structure, may be connected at one side at the plunger and at another side at the pressure line. The bellow structure provides a linear actuating structure that may be controlled pneumatically, hydraulically or electro-mechanically. When using the bellow as a pressure chamber, the pressure in the bellows may linearly or approximate linearly scale with the displacement of the plunger. This way, an accurate correlation between the pressure and the force exerted onto the tissue can be obtained.

Figure 7:
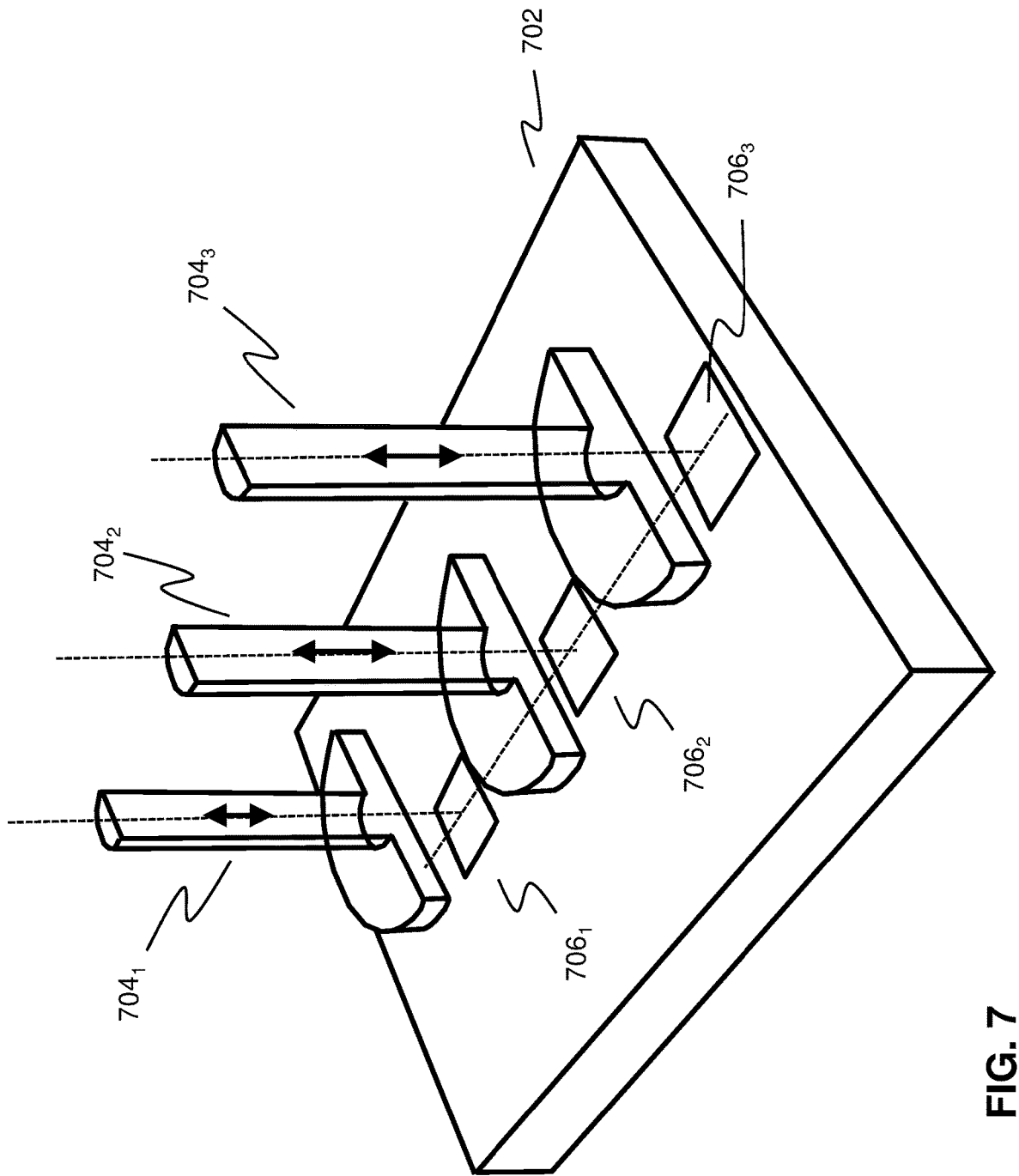
FIG. 7 depicts part of a perfusion measuring device according to yet another embodiment of the invention.

FIG. 7 depicts part of an anastomosis perfusion measuring device according to another embodiment of the invention. In this embodiment, the perfusion measuring device may have a similar structure as described with reference to FIG. 1, however in this embodiment, instead of one actuating structure, the perfusion measuring device may include a plurality of actuating structures $704_{1-4}$. Further, the perfusion measuring device may include a sensor $706_{1-4}$, preferably an optical sensor, for determining the blood perfusion when the actuating structure is controlled by the computer. The actuating structures may include plungers that are slidable along an axis substantially perpendicular to a clamping member. Hence, in this embodiment, a tissue that needs to be tested for an anastomosis may be positioned between the clamping member and the actuating structures. This way, each of the actuating structures may be used to test a different area of the tissue. Hence, a plurality of areas may be tested sequentially by the computer. During testing, each actuating structure may be controlled on the basis of the processes described above with reference to FIG. 4-6. This way, the local viability of a plurality of areas can be tested efficiently. Moreover, if the computer determines that a first test area is not viable for an anastomosis, other areas may be tested without the need to shift the tissue that is clamped.

Figure 8:
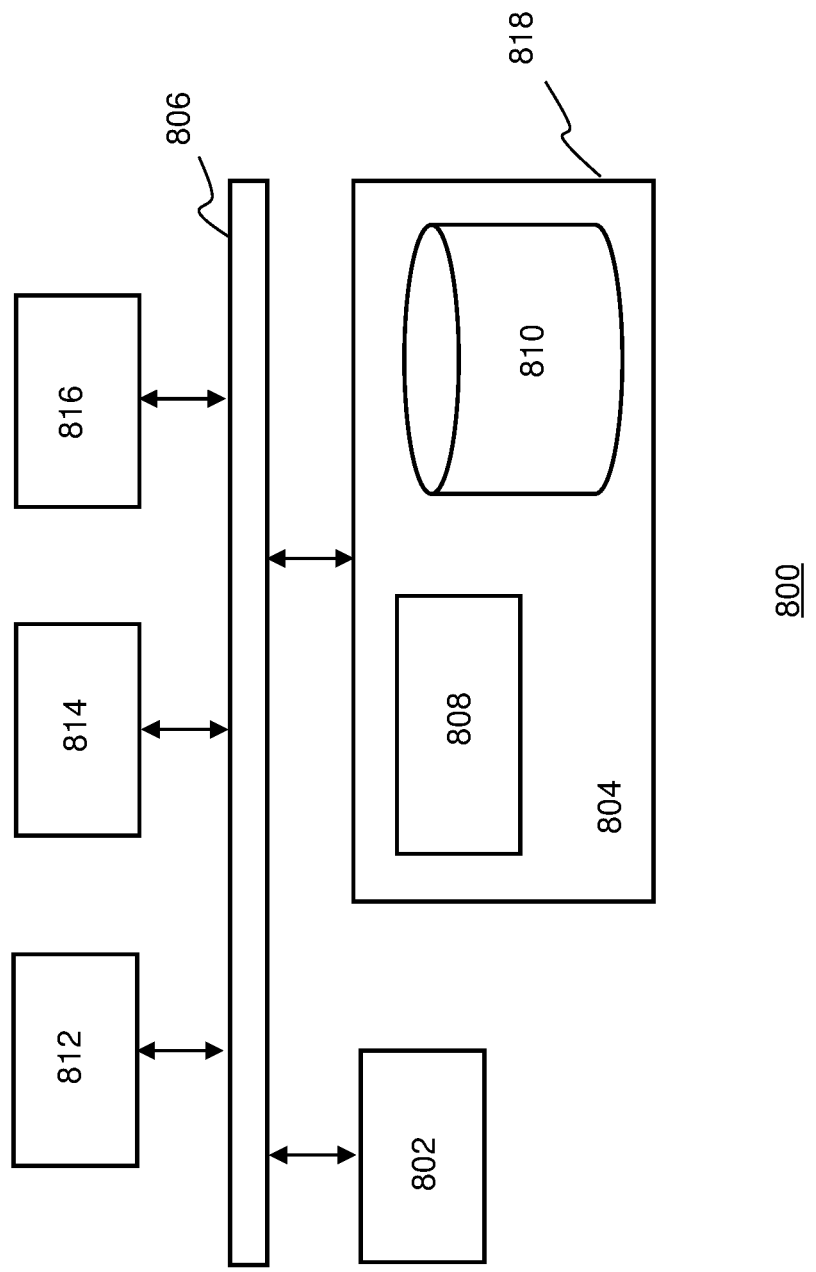
FIG. 8 is a block diagram illustrating an exemplary computer system that may be used for executing methods and software products described in this disclosure.

FIG. 8 is a block diagram illustrating exemplary data processing systems described in this disclosure. Data processing system 800 may include at least one processor 802 coupled to memory elements 804 through a system bus 806. As such, the data processing system may store program code within memory elements 804. Further, processor 802 may execute the program code accessed from memory elements 804 via system bus 806. In one aspect, data processing system may be implemented as a computer that is suitable for storing and/or executing program code. It should be appreciated, however, that data processing system 800 may be implemented in the form of any system including a processor and memory that is capable of performing the functions described within this specification.

Memory elements 804 may include one or more physical memory devices such as, for example, local memory 808 and one or more bulk storage devices 810. Local memory may refer to random access memory or other non-persistent memory device(s) generally used during actual execution of the program code. A bulk storage device may be implemented as a hard drive or other persistent data storage device. The processing system 500 may also include one or more cache memories (not shown) that provide temporary storage of at least some program code in order to reduce the number of times program code must be retrieved from bulk storage device 810 during execution.

Input/output (I/O) devices depicted as input device 812 and output device 814 optionally can be coupled to the data processing system. Examples of input device may include, but are not limited to, for example, a keyboard, a pointing device such as a mouse, or the like. Examples of output device may include, but are not limited to, for example, a monitor or display, speakers, or the like. Input device and/or output device may be coupled to data processing system either directly or through intervening I/O controllers. A network adapter 816 may also be coupled to data processing system to enable it to become coupled to other systems, computer systems, remote network devices, and/or remote storage devices through intervening private or public networks. The network adapter may comprise a data receiver for receiving data that is transmitted by said systems, devices and/or networks to said data and a data transmitter for transmitting data to said systems, devices and/or networks. Modems, cable modems, and Ethernet cards are examples of different types of network adapter that may be used with data processing system 850.

As pictured in FIG. 8, memory elements 804 may store an application 818. It should be appreciated that data processing system 800 may further execute an operating system (not shown) that can facilitate execution of the application. Application, being implemented in the form of executable program code, can be executed by data processing system 500, e.g., by processor 802. Responsive to executing application, data processing system may be configured to perform one or more operations to be described herein in further detail.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A method for testing the viability of a tissue of a patient selected for an anastomosis using a perfusion measuring device comprising steps of:
controlling, by a computer, a number of linear actuating structures of the perfusion measuring device, at least one of the linear actuating structures comprising a slidable pressure plate for exerting a force uniformly downwards onto a first test area of tissue positioned between a surface of the pressure plate and a surface of a clamping member, the surface of the pressure plate being arranged parallel to the surface of the clamping member, the controlling including rapidly ramping up a force uniformly exerted by the pressure plate on the first test area of the tissue selected for the anastomosis, the force uniformly exerted on the first test area defining a local, systolic, perfusion pressure;
receiving by the computer, during the ramping up of the force, a sensor signal from at least one sensor of the perfusion measuring device and a blood pressure signal from a blood pressure measuring device, the sensor signal being indicative of perfusion of blood through micro vascularization in the first test area during the ramping up of the force and the blood pressure signal being indicative of a general, systolic, blood pressure of the patient during the ramping up of the force;
controlling, by the computer, the at least one of the linear actuating structures to slowly ramp down the force uniformly exerted on the first test area, when the at least one sensor signals the computer that the perfusion of the blood in the tissue of the first test area has stopped and,
determining, by the computer, a local perfusion pressure value and a general blood pressure value when, during the ramp down of the force the computer detects a start of the perfusion of the blood through the micro vascularization, wherein the local perfusion pressure value and the general blood pressure value are used for determining a prediction whether or not the tissue of the first test area is viable for an anastomosis, the determined local perfusion pressure value defining a local reperfusion pressure value of the first test area,
determining, by the computer, a prediction whether or not the tissue of the first test area is viable for an anastomosis based on the local reperfusion pressure value of the first test area and the general systolic blood pressure value, by comparing a ratio of the local reperfusion pressure value and the general systolic blood pressure value with a predetermined index value stored in a memory of the computer, wherein the tissue of the first test area is a bowel tissue and the blood pressure signal is indicative of the systolic blood pressure of the patient measured at an arm, and wherein determining, by the computer, the prediction includes steps of:
determining that the bowel tissue of the first test area is viable for an anastomosis if the ratio of the local reperfusion pressure value and the general systolic blood pressure value is equal to or larger than a predetermined bowel-brachial index threshold value, with the threshold value being selected to have a value in a range between 0.1 and 0.5.

2. The method according to claim 1 wherein a first time period for the ramping up of the force from atmospheric pressure to a maximum perfusion pressure value at which minimal or no blood perfusion is measured by the at least one sensor is smaller than a second time period for the ramp down of the force from the maximum perfusion pressure value to the atmospheric pressure.

3. The method according to claim 2, wherein the first time period is between 2 and 20 seconds, and the second time period for the ramp down of the force from the maximum perfusion pressure to the atmospheric pressure is between 3 and 60 seconds.

4. The method according to claim 1 wherein the at least one linear actuating structure includes a pressure chamber connected to the pressure plate, and a pressure in the pressure chamber controls the force exerted onto the first test area of the tissue.

5. The method according to claim 4, wherein the computer controls a pump for controlling a pressure in the pressure chamber.

6. The method according to claim 1, wherein at least one of the linear actuating structures comprises a bellows structure or at least one of the linear actuating structures comprises an expandable balloon structure.

7. The method according to claim 1, wherein the at least one sensor is an optical sensor integrated in the clamping member.

8. The method according to claim 7, wherein the at least one optical sensor is adapted to measure absorption of light emitted onto the tissue of the first test area during the ramping up of the force and the ramp down of the force.

9. The method according to claim 1, wherein:
during at least part of the ramping up of the force and the ramp down of the force, receiving, by the computer, a motion signal of a motion sensor attached to the perfusion measuring device; and,
rejecting or accepting, by the computer, the local reperfusion pressure value based on the motion signal and a predetermined motion threshold value.

10. A non-transitory computer readable storage medium storing software code portions configured for, when run on a computer, executing the method steps according to claim 1.

11. The method according to claim 1, wherein the threshold value is between 0.2 and 0.4.

12. The method according to claim 1, wherein the threshold value is 0.3.

13. A system for testing the viability of a tissue of a patient selected for an anastomosis comprising:
a computer configured for connection to a perfusion measuring device, the computer including a non-transitory computer readable storage medium having computer readable program code stored thereon, and a processor coupled to the computer readable storage medium, wherein the processor is configured to perform executable operations responsive to executing the computer readable program code, the operations comprising:

controlling at least one linear actuating structure of the perfusion measuring device, the at least one linear actuating structure comprising a slidable pressure plate for exerting a force uniformly downwards onto a first test area of tissue positioned between a surface of the pressure plate and a surface of a clamping member, the surface of the pressure plate being arranged parallel to the surface of the clamping member, the controlling including rapidly ramping up the force uniformly exerted by the pressure plate on the first test area of the tissue selected for the anastomosis, the force uniformly exerted on the first test area of the tissue defining a local, systolic, perfusion pressure;

the computer being configured for receiving during the ramping up of the force, a sensor signal from at least one sensor of the perfusion measuring device, and a blood pressure signal from a blood pressure device, the sensor signal being indicative of perfusion of blood through micro vascularization in the first test area of the tissue during the ramping up of the force and the blood pressure signal being indicative of a general, systolic, blood pressure of the patient during the ramping up of the force;

controlling the at least one linear actuating structure to slowly ramp down the force uniformly exerted on the first test area when the sensor signal signals the computer that the perfusion of the blood in the tissue of the first test area has stopped, and, determining a local perfusion pressure value and a general blood pressure value when, during the ramp down of the force, the computer detects a start of perfusion of blood through the micro vascularization, wherein the local perfusion pressure value and the general blood pressure value are used for determining a prediction whether or not the tissue of the first test area is viable for the anastomosis, the determined local perfusion pressure value defining a local reperfusion pressure value of the first test area of the tissue, determining, by the computer, a prediction whether or not the tissue of the first test area is viable for an anastomosis on the basis of the local reperfusion pressure value of the first test area and the general systolic blood pressure value, by comparing a ratio of the local reperfusion pressure value and the general systolic blood pressure value with a predetermined index value stored in a memory of the computer, wherein the tissue is a bowel tissue and wherein the blood pressure signal is indicative of the systolic blood pressure of the patient measured at an arm, and wherein the operation of determining the prediction includes steps of:

determining that the bowel tissue of the first test area is viable for the anastomosis if the ratio of the local reperfusion pressure value and the general systolic blood pressure value is equal to or larger than a predetermined bowel-brachial index threshold value, with the threshold value being selected to have a value in a range between 0.1 and 0.5.

14. The system according to claim 13, wherein a first time period for the ramping up from atmospheric pressure to a maximum perfusion pressure value at which minimal or no blood perfusion is measured by the at least one sensor is smaller than a second time period for the ramp down of the force from the maximum perfusion pressure value to the atmospheric pressure.

15. The system according to claim 14, wherein the first time period is between 2 and 20 seconds, and the second time period for the ramp down of the force from the maximum perfusion pressure to the atmospheric pressure is between 3 and 60 seconds.

16. The system according to claim 13, wherein the at least one linear actuating structure includes a pressure chamber connected to the pressure plate, and a pressure in the pressure chamber controls the force exerted onto the tissue.

17. The system according to claim 16, wherein the computer is configured for controlling a pump to control the pressure in the pressure chamber.

18. The system according to claim 13, wherein the at least one linear actuating structure comprises a bellows structure or the at least one linear actuating structure comprises an expandable balloon structure.

19. The system according to claim 13, wherein the at least one sensor is an optical sensor integrated in the clamping member.

20. The system according to claim 19, wherein the optical sensor is adapted to measure absorption of light emitted onto the tissue of the first test area during the ramping up of the force and the ramp down of the force.

21. The system according to claim 13, wherein the executable operations further comprise steps of:
receiving, by the computer, a motion signal of a motion sensor attached to the perfusion measuring device during at least part of the ramping up of the force and the ramp down of the force; and,
rejecting or accepting, by the computer, the local reperfusion pressure value on the basis of the motion signal and a predetermined motion threshold value.

22. The system according to claim 13, wherein
the perfusion measuring device comprises a plurality of the linear actuating structures and one or more of the at least one sensor associated with each of the linear actuating structures, wherein the linear actuating structures include pressure plates configured to exert a force uniformly downwards onto different test areas of a tissue that are each positioned between one of the linear actuating structures and the clamping member of the perfusion measuring device, the surface of each of the pressure plates being arranged parallel to the surface of the clamping member and wherein the one or more sensors are configured to determine a signal that is indicative of perfusion of blood through the micro vascularization in each of the different test areas;
wherein the computer is connected to each of the plurality of linear actuating structures of the perfusion measuring device.

23. The system according to claim 13, wherein the threshold value is between 0.2 and 0.4.

24. The system according to claim 13, wherein the threshold value is 0.3.

* * * * *